United States Patent [19]

Bauer et al.

[11] 4,261,888
[45] Apr. 14, 1981

[54] ORGANIC COMPOUNDS

[75] Inventors: Wilfried Bauer, Lampenberg; Francois Cardinaux; Rene Huguenin, both of Reinach; Janos Pless, Basel; Edmond Sandrin, Riehen, all of Switzerland

[73] Assignee: Sandoz Ltd., Basel, Switzerland

[21] Appl. No.: 97,630

[22] Filed: Nov. 27, 1979

Related U.S. Application Data

[60] Division of Ser. No. 856,617, Dec. 2, 1977, which is a continuation of Ser. No. 762,646, Jan. 26, 1977, abandoned.

[30] Foreign Application Priority Data

Apr. 12, 1976 [CH] Switzerland .......................... 5931/76
Apr. 29, 1976 [CH] Switzerland .......................... 5447/76
Jul. 19, 1976 [CH] Switzerland .......................... 9207/76

[51] Int. Cl.$^3$ ........................................... C07C 103/52
[52] U.S. Cl. ............................................ 260/112.5 R
[58] Field of Search .................. 424/177; 260/112.5 R

[56] References Cited

FOREIGN PATENT DOCUMENTS 2703109 4/1977 Fed. Rep. of Germany .... 260/112.5 R
2741393 3/1978 Fed. Rep. of Germany .... 260/112.5 R Primary Examiner—Delbert R. Phillips
Attorney, Agent, or Firm—Gerald D. Sharkin; Robert S. Honor; Thomas O. McGovern

[57]  ABSTRACT

The invention provides polypeptides of formula I,

A-B-Gly-D-E    I wherein A is Tyr or substituted Tyr,
B is -Gly- or -(D)Ala-,
D is, for example, Phe or MePhe and
E is, for example, -Met-X, -Leu-X, -Nle-X, -Nva-X, -Ile-X, methioninesulhoxide-X, methioninesulphone-X wherein X is —NR'R" or —OR'" and each of R', R" and R'" independently signifies hydrogen or alkyl of 1 to 5 carbon atoms, which compounds possess pharmacological activity, for example, analgesic activity.

1 Claim, No Drawings

ORGANIC COMPOUNDS

This application is a divisional application of our copending application Ser. No. 856,617 filed Dec. 2, 1977 which in turn is a continuation application of our application Ser. No. 762,646 filed Jan. 26, 1977 now abandoned.

The present invention relates to polypeptide derivatives.

More particularly, the present invention provides compounds of formula I,

A—B—Gly—D—E     I wherein A is a residue of formula

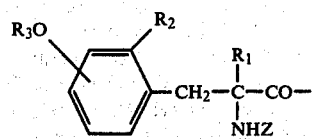

wherein
$R_1$ is hydrogen or alkyl of 1 to 4 carbon atoms,
$R_2$ is hydrogen or, together with $R_1$, forms an ethylene bridge, and
$R_3$ is hydrogen, alkyl of 1 to 4 carbon atoms or an $R_4CO-$ group,
wherein $R_4$ is a saturated or unsaturated branched or unbranched alkyl residue of 1 to 17 carbon atoms, phenyl or phenylalkyl of 7 to 12 carbon atoms in which the phenyl residue can be mono- or disubstituted with fluorine, chlorine or bromine, alkyl of 1 to 4 carbon atoms or alkoxy of 1 to 4 carbon atoms, whereby the $R_3O$ groups is in a position meta- or para- to the

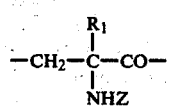

residue,
Z is hydrogen, alkyl of 1 to 5 carbon atoms, alkenyl of 3 to 5 carbon atoms, cyclopropylmethyl, cyclobutylmethyl, $R_4CO$, wherein $R_4$ is as previously defined, H-Arg, H-Lys, H-Phe or H-Tyr,
B is —Gly— or —(D)Ala—,
D is a residue of formula

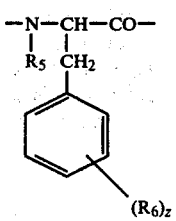

wherein
$R_5$ is hydrogen or alkyl of 1 to 4 carbon atoms,
$R_6$ is hydrogen, fluorine, chlorine, bromine, nitro, alkyl of 1 to 4 carbon atoms or alkoxy of 1 to 4 carbon atoms, and
z is 1 or 2,
E is (i) -Met-X, -Leu-X, -Nle-X, -Nva-X, -Ile-X, or

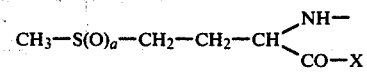

(a = 1 or 2)

wherein X is

or $-OR'''$ and each of R', R", and R''' independently signifies hydrogen or alkyl of 1 to 5 carbon atoms, or
(ii) a residue of formula

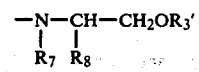

wherein
$R_3'$ is hydrogen or $R_4CO-$, wherein $R_4$ is as previously defined,
$R_7$ is hydrogen or alkyl of 1 to 4 carbon atoms, and
$R_8$ is
(a)

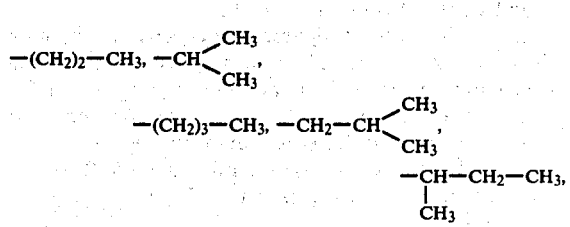

(b) $-(CH_2)_m-CH_2OR_3'$ wherein $R_3'$ is as previously defined, and m is from 0 to 6,
(c)

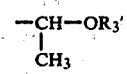

wherein $R_3'$ is as previously defined,
(d) $-CH_2-S-H$,
(e)

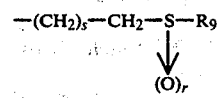

wherein $R_9$ is alkyl of 1 to 5 carbon atoms, r is 0, 1 or 2, and s is 0, 1 or 2,
(f) $-(CH_2)_4-NH_2$, $-(CH_2)_4-NHCOR_4$, wherein $R_4$ is as previously defined,

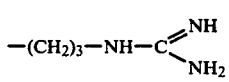

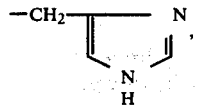

-continued (f) 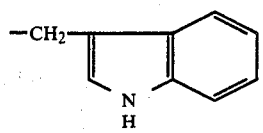

(g) —(CH$_2$)$_n$—CONH$_2$, wherein n is 1 or 2, (h) —(CH$_2$)$_n$—COOR$_{10}$, wherein n is as previously defined, and R$_{10}$ is hydrogen or alkyl of 1 to 5 carbon atoms, or (iii) a residue of formula

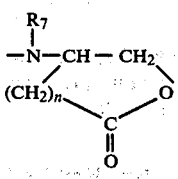

wherein n and R$_7$ are as previously defined, whereby the A and D residues possess either the L- or D,L- configuration and the residue E possesses the L-, D- or D,L- configuration, provided that the residue B can only signify -Gly- when, (a) R$_1$, in residue A, is alkyl or together with R$_2$ forms an ethylene bridge and/or Z is cyclopropyl or cyclobutylmethyl, and/or (b) D is other then Phe, and/or (c) E has a significance other than those defined under (i) and other than leucinolnorleucinol-, isoleucinol, norvalinol or methioninol residues in free form or in the form of the esters derived from R$_4$COOH, wherein R$_4$ is as previously defined.

When R$_1$ is alkyl, this is preferably methyl. R$_1$ preferably is hydrogen or, together with R$_2$, forms an ethylene bridge.

When R$_3$ is alkyl, this is preferably methyl.

R$_3$ especially signifies hydrogen.

R$_3$O is preferably in a position para- to the

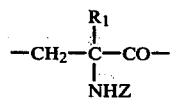

residue.

Z is preferably hydrogen.

B is preferably -(D)Ala-.

When R$_5$ is alkyl, this is preferably methyl.

R$_5$ is preferably methyl or hydrogen.

R$_6$ is preferably hydrogen, nitro or chlorine, especially hydrogen or nitro.

As an aminoacid residue, E is preferably methionine, methioninesulphoxide or methioninesulphone, especially methioninesulphoxide.

X is preferably

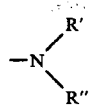

especially —NH$_2$.

R$_7$ is especially hydrogen.

R$_8$ is preferably hydrogen.

R$_9$ is preferably methyl.

r is preferably 1 or 2, especially 1.

s is preferably 0 or 1, especially 1.

n is preferably 2.

E is preferably an acid amide as defined under (i) or a residue as defined under (ii) and (iii), especially a residue as defined under (ii) and (iii).

When E is a residue as defined under (ii), the residues indicated under (e) wherein r is 1 or 2, more preferably 1, and s is 0 or 1, more preferably 1, are especially preferred.

The residues defined for E preferably have the L-configuration.

In one group of compounds, R$_4$ is alkyl of 1 to 17 carbon atoms, suitably 1 to 12 carbon atoms, conveniently from 1 to 6 carbon atoms, for example, methyl, ethyl, propyl and butyl. When R$_4$ is alkyl of two or more carbon atoms, this moiety may be unsaturated. When R$_4$ is alkyl of three or more carbon atoms, the moiety may be branched and optionally unsaturated.

When R$_4$ is phenyl or phenylalkyl of 7 to 12 carbon atoms, e.g. tolyl and benzyl, the phenyl residue may be mono- or disubstituted with fluorine, chlorine or bromine. The phenyl residue may also be substituted with alkyl of 1 to 4 carbon atoms or alkoxy of 1 to 4 carbon atoms.

In a second group of compounds, Z is hydrogen, alkyl of 1 to 5 carbon atoms, alkenyl of 3 to 5 carbon atoms, cyclopropylmethyl or cyclobutylmethyl.

In a third group of compounds, Z is R$_4$CO, wherein R$_4$ is as previously defined.

In a fourth group of compounds, Z is H-Arg-, H-Lys-, H-Phe- or H-Tyr-.

In a fifth group of compounds, R$_6$ is hydrogen, fluorine, chlorine, bromine or nitro.

In a sixth group of compounds, R$_6$ is alkyl of 1 to 4 carbon atoms or alkoxy of 1 to 4 carbon atoms.

In a seventh group of compounds, E as previously defined under (i) is Met-X, -Leu-X, -Nle-X, -Nva-X, -Ile-X, -methioninesulphoxide-X, or -methioninesulphone-X, wherein X is —NR'R" as previously defined. In another group of compounds, X is —OR''' as previously defined.

In an eighth group of compounds, E as previously defined under (i) is

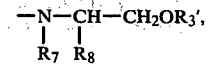

wherein R$_3$' and R$_7$ are as previously defined and R$_8$ is as previously defined under (a), (b) and (c). In another group of compounds, R$_8$ is as previously defined under (d) and (e). In a further group of compounds, R$_8$ is —(CH$_2$)$_4$—NH$_2$, —(CH$_2$)$_4$—NHCOR$_4$, wherein R$_4$ is as previously defined, or R$_8$ is as previously defined under (g) and (h). In three further groups of compounds, R$_8$ is

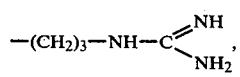

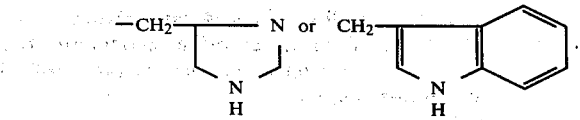

In a ninth group of compounds, E is as previously defined under (iii).

A peptide of formula I may be obtained by methods which are conventional in the art of peptide synthesis.

Accordingly, the present invention provides a process for the production of a peptide of formula I which comprises (a) removing at least one protective group from a protected peptide having the sequence indicated in formula I, or (b) linking together by an amide bond two peptide units, each of which contains at least one aminoacid and which is in protected or unprotected form, the peptide units being such that the aminoacid sequence given in formula I is obtained, and then, if necessary, effecting process variant (a), or (c) converting a group A and/or E of an unprotected or protected peptide into another group A and/or E having the definition previously indicated, and, if necessary, effecting process variant (a).

The above methods are known in peptide chemistry and may be effected in manner analogous to the processes described in the following Examples.

Insofar as the production of the starting materials is not particularly described, these compounds are known or may be produced and purified in accordance with known methods. These compounds may also be produced in a manner analogous to the processes described in the following Examples.

The compounds may exist in salt, including acid addition salt, forms or in the form of complexes, for example, complexes with metals.

Suitable acids for acid addition salt formation are acetic acid, trifluoroacetic acid and hydrochloric acid.

Suitable metals for complex formation include calcium, magnesium, aluminium, cobalt and especially zinc.

In the following Examples, all temperatures are indicated in degrees Celsius.

| | |
|---|---|
| Ac | = acetyl |
| Boc | = tert.-butyloxycarbonyl |
| Bzl | = benzyl |
| DMF | = dimethylformamide |
| Me | = methyl |
| TFA | = trifluoroacetic acid |
| AcTyr | = N-acetyltyrosyl |
| Ata(6-OH) | = 2-amino-6-hydroxy-2-tetralin-carboxylic acid |
| Ata(7-OH) | = 2-amino-7-hydroxy-2-tetralin-carboxylic acid |
| EtPhe | = N-ethylphenylalanyl |
| MePh | = N-methylphenylalanyl |
| MeTyr | = N-methyltyrosyl |
| Phe(p-Cl) | = p-chlorophenylalanyl |
| Phe(3,4-diMeO) | = 3,4-dimethoxyphenylalanyl |
| Phe(p-NO$_2$) | = p-nitrophenylalanyl |
| m-Tyr | = m-tyrosyl |
| Tyr(Ac) | = O-acetyltyrosyl |
| Tyr(Me) | = O-methyltyrosyl |
| Tyr(Piv) | = O-pivaloyltyrosyl |
| α-Me-Tyr | = α-methyltyrosyl |
| decomp | = decomposition temperature. |

EXAMPLE 1:

H-Tyr-(D)Ala-Gly-Phe-methioninol (TFA)

2.0 g of Boc-Tyr-(D)Ala-Gly-Phe-methioninol are dissolved in 20 ml of TFA-CH$_2$Cl$_2$ (1:1) and left to stand for 30 minutes at 0°. After reducing the volume under vacuum, the title compound is precipitated with ether and filtered off. The title compound is obtained as an amorphous salt.

$[\alpha]_D^{20} = +25°$ (c=2.1 in 95% acetic acid).

The Boc-Tyr-(D)Ala-Gly-Phe-methioninol, used as starting material, is produced as follows:

(a) Boc-Phe-methioninol 2.9 g of Boc-Phe-OH and 1.4 ml of N-ethylmorpholine are dissolved in 50 ml of absolute tetrahydrofuran and 1.4 ml of chloroformic acid iso-butyl ester added at −10°. After 10 minutes, a solution of 1.7 g of methioninol-hydrochloride in 25 ml of dimethyl formamide is added. After two hours stirring at room temperature, the solution is evaporated under vacuum and the residue taken up in acetic acid. The solution is repeatedly washed with dilute citric acid and potassium bicarbonate and the title compound isolated. M.P. 106°.

$[\alpha]_D^{20} = -24$ (c=2.0 in DMF).

(b) H-Phe-methioninol.trifluoroacetate 3.8 of Boc-Phe-methioninol are left to stand for 1 hour at room temperature in 50 ml of a mixture of trifluoroacetic acid/1-chlorobutane (1:1). Finally, the solution is evaporated to dryness, pulverised in a mixture of ether/petroleum ether (1:2) and used directly for the coupling reaction.

(c) Boc-(D)Ala-Gly-OBzl 1.9 g of Boc-(D)Ala-OH and 1.3 ml of N-ethylmorpholine are dissolved in 50 ml of absolute tetrahydrofuran and 1.3 ml of chloroformic acid iso-butyl ester added dropwise at a temperature of −15°. After 5 minutes, a solution of 3.4 g of glycine-benzylester-tosylate and 1.3 ml of N-ethylmorpholine in 50 ml of DMF is added. After 1 hour's stirring at −10°, the reaction mixture is evaporated and the residue taken up in acetic acid. The solution is repeatedly washed with dilute citric acid and potassium bicarbonate. The title compound is crystallised from ether. M.P. 88°.

$[\alpha]_D^{20} = 11.6°$ (c=2.0 in DMF).

(d) H-(D)Ala-Gly-OBzl.hydrochloride 3.4 g of Boc-(D)Ala-Gly-OBzl are dissolved in 50 ml of dioxane containing HCl and left to stand for one hour. The volume of the solution is reduced under vacuum and an excess of ether added. The precipitated salt is filtered off, dried and used as such for the coupling reaction.

(e) Boc-Tyr-(D)Ala-Gly-OBzl 2.8 g of Boc-Tyr-OH and 1.3 ml of N-ethylmorpholine are dissolved in 50 ml of absolute tetrahydrofuran and 1.3 ml of chloroformic acid iso-butyl ester are added dropwise at −15°. After 5 minutes, a solution of 2.7 g of HCl.H-(D)Ala-Gly-OBzl and 1.3 ml of N-ethylmorpholine in 20 ml of DMF are added. After 1 hour's stirring at −10°, the mixture is worked up in the manner indicated under (c) above. The title compound is crystallised from methanol/petroleum ether. Decomp. 65°.

$[\alpha]_D^{20} = 35.0°$ (c=1.5 in methanol).

(f) Boc-Tyr-(D)Ala-Gly-OH 12 g of Boc-Tyr-(D)Ala-Gly-OBzl are dissolved in a mixture of methanol/H$_2$O (9:1) and hydrogenated in the presence of Pd-C at normal pressure and room temperature. The mixture is fitered off from the catalyst, reduced in volume and crystallised from methanol/CH$_2$CL$_2$/ether. Decomp. 110°.

$[\alpha]_D^{20} = 22°$ (c=1.07 in 95% acetic acid).

(g) Boc-Tyr-(D)Ala-Gly-Phe-methioninol 4.1 g of Boc-Tyr-(D)Ala-Gly-OH and 1.1 ml of N-methyl-morpholine are dissolved in 50 ml of absolute tetrahydrofuran and 1.0 ml of chloroformic acid ethyl ester added dropwise at $-15°$. After 5 minutes, a solution of 4.0 g of H-Phe-methioninol trifluoroacetate and 1.2 ml of N-methylmorpholine in 50 ml of DMF is added. After 1 hour's stirring at 0°, the reaction mixture is evaporated and the residue taken up in acetic acid. The solution is repeatedly washed with 10% phosphoric acid and 1 N sodium bicarbonate. After evaporation of the acetic esters, the residue is crystallised from methanol/ether. M.P. 158°.

$[\alpha]_D^{20} = -18°$ (c=0.7 in DMF).

EXAMPLE 2

O,O'-Di-acetyl-Tyr-(D)Ala-Gly-Phe-methioninol.trifluoroacetate 0.57 g of H-Tyr-(D)Ala-Gly-Phe-methioninol. TFA are dissolved in 6 ml of trifluoroacetic acid and 0.5 ml of acetylchloride added dropwise. The mixture is stirred for 2 hours at room temperature, evaporated at 25° and the residue triturated in 50 ml of ether. The powder obtained is filtered off by vacuum filtration, washed with ether and dried.

$[\alpha]_D^{20} = 24°$ (c=0.5 in 95% acetic acid).

EXAMPLE 3

H-Tyr-(D)Ala-Gly-MePhe-methioninsulphone.trifluoroacetate

A mixture of 0.18 g of Boc-Tyr-(D)Ala-Gly-MePhe-methioninosulphone in 2 ml of $CH_2Cl_2$ and 0.33 ml of anisole is cooled and 10 ml of 98% trifluoroacetic acid added. The mixture is left to stand at room temperature for 30 minutes, the volume reduced under vacuum and the concentrate added dropwise, with stirring, to 130 ml of ether. The precipitated product is centrifuged off. The residue is recrystallised twice from ether, dissolved in water and lyophilised. The title compound is obtained.

$[\alpha]_D^{20} = -3.5°$ (c=1.7 in 95% acetic acid).

The Boc-Tyr-(D)Ala-Gly-MePhe-methioninolsulphone employed as starting material may be prepared as follows:

(a) Boc-MePhe-OH 3.6 g of H-MePhe-OH are dissolved in a mixture of ter.-butanol, 25 ml of 10% aqueous $KHCO_3$ solution and 5 ml of 4 N sodium hydroxide. 8 ml of di-tert.-butyl-carbonate are added and the mixture stirred for 2 days at room temperature. The reaction mixture is diluted with ca. 100 ml of water and extracted with ether. The aqueous phase is acidified, with stirring to pH 2. The precipitated product is extracted with acetic acid, the extract washed with water and dried over $Na_2SO_4$. The liquid is evaporated and the product crystallised from ether/petroleum ether to yield Boc-MePHe-OH. M.P. 87°.

$[\alpha]_D^{20} = -65°$ (c=1 in methanol).

(b) Boc-MePhe-methioninol 3.1 g of Boc-MePhe-OH are dissolved in 30 ml of tetrahydrofuran, cooled to $-20°$, and 1.45 ml of N-ethylmorpholine are added with stirring followed by 1.45 ml of chloroformic acid iso-butyl ester and the mixture stirred for a further 5 minutes at $-20°$. A cold solution of 1.80 g of methioninol in 1 ml of tetrahydrofuran is added, the mixture left to stand for 2 hours at a temperature of from $-5°$ to 0° and then stirred for 2 hours at room temperature. The reaction mixture is diluted with ca. 350 ml of acetic acid and washed repeatedly with water, 1 N citric acid, 10% $KHCO_3$ and 30% NaCl solution. The organic phase is dried over $Na_2SO_4$ and evaporated, whereby Boc-MePhe-methioninol is obtained as an amorphous product.

$[\alpha]_D^{20} = -54°$ (c=1.24 in methanol).

(c) H-MePhe-methioninol.trifluoroacetate

To a solution of 4.3 g of Boc-MePhe-methioninol in 20 ml of $CH_2Cl_2$, 5 ml of $CH_3-S-CH_2-CH_3$ and 0.2 ml of $HS-CH_2-CH_2OH$ are added 40 ml of 98% TFA at 0°. The reaction mixture is left to stand for 1½ hours and thereafter the volume is reduced in vacuo to 5-10 ml and precipitated twice from ether/petroleum ether. The oily product is dried under high vacuum, whereby H-MePhe-methioninol.trifluoroacetate is obtained as an amorphous product.

$[\alpha]_D^{20} = 3.2°$ (c=0.98 in methanol)

(d) Boc-Tyr-(D)Ala-Gly-MePhe-methioninol 1.23 g of Boc-Tyr-(D)Ala-Gly-OH is dissolved in 30 ml of THF and cooled to 15°. 0.38 ml of ethylmorpholine are added with stirring followed by 0.39 ml of chloroformic acid iso-butyl ester and stirring continued for 10 minutes. A cold solution of 14 g of TFA.H-MePhe-methioninol and 0.45 ml of N-ethylmorpholine in 12 ml of TFA are added with stirring at $-15°$. The mixture is stirred for 20 hours at 0°, diluted with 250 ml of acetic acid and washed repeatedly with water, 1 N citric acid, 10% $KHCO_3$ and 30% NaCl solution. The liquid is dried over $Na_2SO_4$ and evaporated. The residue is purified chromatographically on kieselgel using a mixture of methanol/$CH_2Cl_2$/50% acetic acid, whereby the title compound is obtained. Decomp. 160°.

$[\alpha]_D^{20} = 50°$ (c=1.8 in DMF).

(e) Boc-Tyr-(D)Ala-Gly-MePhe-methioninosulphone 0.25 g of Boc-Tyr-(D)Ala-Gly-MePhe-methioninol are dissolved in 3 ml of 90% acetic acid and 0.4 ml of 10 M $H_2O_2$ added. The mixture is left to stand for 24 hours at room temperature and then evaporated under vacuum. The residue is purified chromatographically on kieselgel using a mixture of $CH_2Cl_2$/methanol/50% acetic acid, whereby the title compound is obtained.

$[\alpha]_D^{20} = -33.8°$ (c=0.93 in dimethylformamide).

EXAMPLE 4

H-Tyr-(D)Ala-Gly-MePhe-methioninol.trifluoroacetate

A mixture of 0.28 g of Boc-Tyr-(D)Ala-Gly-MePhe-methioninol, 0.47 ml of thioanisole and 0.1 ml of HS-$CH_2$-$CH_2$-OH in 1 ml of $CH_2Cl_2$ are cooled and 10 ml of TFA are added. The mixture is left to stand for 45 minutes at room temperature, the volume reduced under vacuum and the concentrate added, with stirring, to 130 ml of ether. The mixture is centrifuged and the residue is dissolved in water and lyophilised, whereby the title compound is obtained.

$[\alpha]_D^{21} = -4.2$ (c=0.25 in 95% acetic acid).

EXAMPLE 5

H-Tyr-(D)Ala-Gly-MePHe-methioninolsulphoxide.trifluoroacetate

A mixture of 0.18 g of Boc-Tyr-(D)Ala-Gly-MePhe-methioninolsulphoxide in 2 ml of $CH_2Cl_2$ and 0.33 ml of anisole are cooled and 10 ml of 98% TFA added. The mixture is left to stand for 30 minutes at room temperature, the volume reduced under vacuum and the concentrate added dropwise, with stirring, to 130 ml of ether. The precipitated product is centrifuged off. The residue is recrystallised twice from ether, dissolved in water and lyophilised, whereby the title compound is obtained.

$[\alpha]_D^{20} = -4°$ (c=2.05 in 95% acetic acid).

The Boc-Tyr-(D)Ala-Gly-MePhe-methioninolsulphoxide used as starting material may be prepared as follows:

0.32 g of Boc-Tyr-(D)-Ala-Gly-MePhe-methioninol are dissolved in 4 ml of 90% acetic acid and 0.07 ml of 10 M $H_2O_2$ is added. The mixture is left to stand for 3 hours at room temperature and reduced in volume under vacuum. The residue is purified chromatographically on kieselgel using a mixture of $CH_2Cl_2$/methanol/50% acetic acid, whereby the amorphous title compound is obtained.

$[\alpha]_D^{20} = -36°$ (c=1.74 in dimethylformamide).

The following compounds can be prepared in manner analogous to those illustrated in the foregoing Examples, using appropriate starting materials in approximately equivalent amounts.

All the amino residues, with the exception of glycyl, as well as the aminoalcohols, with the exception of serinol, possess the L- configuration unless otherwise stated. An aminoalcohol is indicated as belonging to the L- series when the —$CH_2$-OH is in the position occupied by the α-COOH group in the aminoacid concerned. In the case of the lactone previously defined under (iii) (Example No. 14), the same rule applies in the case of lactones, previously defined under (iii), which have been hydrolytically opened.

TABLE 1

Compounds of Formula I: H—Tyr—(D)Ala—Gly—Phe—E

| Ex. No. | H—E | Salt Form | $[\alpha]_D^{20}$ | c in AcOH 95% |
|---|---|---|---|---|
| 6 | Methionine | TFA | +26.4° | 1.2 |
| 7 | Methioninosulphoxide | — | +22.7° | 0.6 |
| 8 | Asparaginol | TFA | +39.6° | 1 |
| 9 | D-Methioninol | — | +23.1° | 1.3 |
| 10 | D-Methioninolsulphoxide | AcOH | +20.9° | 1.3 |
| 11 | Glutaminol | TFA | +44.8° | 1 |
| 12 | Serinol | TFA | +52.7° | 1 |
| 13 | 2-Amino-1,4-dihydroxybutane | TFA | +38.5° | 1 |
| 14 | 3-Aminobutyrolactone | TFA | +37.2° | 1 |
| 15 | S-Methylcysteinol | TFA | −16.6° | 1.2 |
| 16 | S-Methylcysteinolsulphoxide | TFA | +3.4° | 1.2 |
| 17 | Leucinol | TFA | +40.5° | 1 |
| 18 | Histidinol | TFA | +37.1° | 1 |
| 19 | N-Methylmethioninesulphoxide | HCl | +27° | 0.4 |
| 20 | N-Methylmethioninesulphone | HCl | +30° | 0.5 |

TABLE 2

Compounds of Formula I: H—Tyr—(D)Ala—Gly—D—E

| Ex. No. | D | H—E | Salt Form | $[\alpha]_D^{20}$ | c in AcOH 95% |
|---|---|---|---|---|---|
| 21 | D,L-Phe(p-Cl) | Methioninol | TFA | +23.2° | 0.98 |
| 22 | D,L-Phe(p-Cl) | Methioninolsulphoxide | TFA | +25.2° | 1.0 |
| 23 | Phe(p-$NO_2$) | Methioninol | AcOH | +23° | 0.65 |
| 24 | Phe(p-$NO_2$) | Methioninolsulphoxide | TFA | +31° | 0.24 |
| 25 | Phe(p-$NO_2$) | Methioninolsulphone | TFA | +7.3° | 0.8 |
| 26 | MePhe | S-Methylcysteinolsulpoxide | HCl | −39° | 1 |
| 27 | Phe(3,4-diMeO)* | Methioninolsulphoxide | TFA | +22.1° | 0.76 |
| 28 | Phe(3,4-diMeO)* | Methioninolsulphoxide | TFA | +29.4° | 0.89 |
| 29 | EtPhe | Methioninol | AcOH | −8.3° | 0.7 |
| 30 | MePhe(p-$NO_2$) | Methioninol | TFA | −9.8° | 1.0 |
| 31 | MePhe(p-$NO_2$) | Methioninolsulphoxide | TFA | −10.4° | 1.3 |
| 32 | MePhe | Methioninamide | TFA | +5.4° | 0.65 |
| 33 | MePhe | Methioninamidesulphoxide | TFA | −3.4° | 0.89 |

*Of uniform configuration which has not been determined. Isomers chromatographically separated on kieselgel.

TABLE 3

Compounds of Formula I: A—(D)Ala—Gly—D—E

| Ex. No. | A | D | H—E | Salt Form | $[\alpha]_D^{20}$ | c in AcOH 95% |
|---|---|---|---|---|---|---|
| 34 | H—D,L-Ata(6-OH) | Phe | Methioninol | HCl | −8.8°[1] | 1.2 |
| 35 | H—Tyr(Piv) | Phe | Methioninolpivaloate | — | +19° | 0.6 |
| 36 | H—D,L-Ata(6-OH) | Phe | Methioninolsulphoxide | HCl | −0.7° | 1 |
| 37 | H—D,L-Ata(6-OH) | MePhe | Methioninol | TFA | −43.6° | 1.1 |
| 38 | H—D,L-Ata(6-OH) | MePhe | Methioninolsulphoxide | TFA | −39.8° | 1 |
| 39 | H—Tyr(Me) | MePhe | Methioninolsulphoxide | HCl | −16.9° | 1.1 |
| 40 | H—Arg—Tyr | MePhe | Methioninolsulphoxide | 2AcOH | −5.4°[2] | 1.1 |
| 41 | N-Cyclobutyl-methyl-Tyr | MePhe | Methioninolsulphoxide | HCl | −13.2° | 0.9 |
| 42 | H—D,L-Ata(7-OH) | MePhe | Methioninolsulphoxide | HCl | −39° | 0.9 |
| 43 | MeTyr | MePhe | Methioninolsulphoxide | HCl | −13.5° | 1.1 |
| 44 | H—D,L-m-Tyr | MePhe | Methioninolsulphoxide | HCl | −30.5° | 1.2 |
| 45 | AcTyr | MePhe | Methioninolsulphoxide | — | — | — |

[1] $[\alpha]_D^{22}$
[2] $[\alpha]_D^{21}$
[3] in DMF

TABLE 4

| | Compounds of Formula I: A—Gly—Gly—Phe—E | | | |
|---|---|---|---|---|
| Ex. No. | A | H—E | $[\alpha]_D^{20}$ | c in AcOH 95% |
| 46 | H—D,L-Ata(6-OH) | Methionine | −5.5°[1] | 1 |
| 47 | H—D,L-m-Tyr | Methionine | +1.5° | 0.6 |
| 48 | H—D,l-α-Me—Tyr | Methionine | 0° | 2.5 |

[1] $[\alpha]_D^{22}$

The compounds of formula I are useful because they possess pharmacological activity in animals. In particular, the compounds are useful as analgesic agents for the treatment of pain as indicated in standard tests, e.g. in the Tail Flick Test in mice on i.v., s.c. or p.o. administration of from 0.5 to 100 mg/kg animal body weight of the compounds, in the Randall Selitto Test in rats on s.c. administration of from 0.5 to 2 mg/kg animal body weight of the compounds and in the Shock Titration Test in he rhesus monkey on s.c. and i.v. administration of from 2.0 to 4 mg/kg animal body weight of the compounds.

Additionally, observations in mice show that the compounds of formula I inhibit spontaneous motor activity in mice on s.c. and p.o administration of from 1.0 to 100 mg/kg animal body weight, causing hypothermia, sedation and inducing catalepsy. The compounds therefore exhibit properties characteristic of anti-psychotic agents, for example, neuroleptics, and are therefore useful as anti-psychotic agents.

For these uses, the dosage will, of course, vary depending on the compound employed, mode of administration and treatment desired. However, in general, satisfactory results are obtained when administered at a daily dosage of from 0.5 to 100 mg/kg animal body weight, conveniently given in divided doses 2 to 4 times a day or in sustained release form. For the larger animals, the total daily dosage is in the range of from about 30 to about 300 mg, and dosage forms suitable for oral administration comprise from about 7 mg to about 150 mg of the compounds admixed with a solid or liquid pharmaceutical carrier or diluent.

The compounds may be administered in pharmaceutically acceptable salt forms, including acid addition salt forms, or in the form of complexes. Such forms exhibit the same order of activity as the free base forms and are readily prepared in conventional manner. Representative acids for acid addition salt forms include organic acids such as trifluoroacetic acid and mineral acids such as hydrochloric acid. Suitable metals for complex formation include zinc. The present invention also provides a pharmaceutical composition comprising a compound of formula I, in free base form or in the form of a pharmaceutically acceptable salt or complex, in association with a pharmaceutically acceptable carrier or diluent. Such compositions may be in the form of, for example, a solution of a capsule.

In one group of compounds, $R_1$ and $R_2$ are as defined, $R_3$ is hydrogen or an $R_4CO$ group as defined, Z is hydrogen, alkyl of 1 to 5 carbon atoms, alkenyl of 3 to 5 carbon atoms, cyclopropylmethyl or $R_4CO$ as previously defined, B is as defined, D is Phe or MePhe and E is methioninesulphone-X, wherein X is

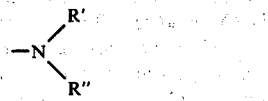

or —OR‴ and each of R′, R″ and R‴ independently signifies hydrogen or alkyl of 1 to 5 carbon atoms.

In a preferred group of compounds, $R_1$, $R_2$, $R_3$, $R_4$, Z, B and D are as defined for the previous group of compounds and E is —Met—X, —Leu—X, —Nle—X, —Nva—X, —Ile—X, methioninesulphoxide-X wherein X is

or OR‴ and each of R′, R″, and R‴ independently signifies hydrogen or alkyl of 1 to 5 carbon atoms.

What is claimed is:
1. Boc-Tyr-(D)-Ala-Gly-OH.